United States Patent
Alfekri et al.

(10) Patent No.: US 9,506,853 B2
(45) Date of Patent: Nov. 29, 2016

(54) AIR FLOW DEVICE

(71) Applicant: Hewlett-Packard Development Company, L.P., Fort Collins, CO (US)

(72) Inventors: Dheya M. Alfekri, San Diego, CA (US); Ronald J. Selensky, San Diego, CA (US); Mark Drake, San Diego, CA (US); Manuel Olmos Lara, Jr., San Diego, CA (US); Marlene Borowinski, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 588 days.

(21) Appl. No.: 13/872,649

(22) Filed: Apr. 29, 2013

(65) Prior Publication Data
US 2014/0318283 A1    Oct. 30, 2014

(51) Int. Cl.
*G01N 17/00*    (2006.01)

(52) U.S. Cl.
CPC .................................... *G01N 17/00* (2013.01)

(58) Field of Classification Search
CPC ..................................................... G01N 17/00
See application file for complete search history.

(56) References Cited

U.S. PATENT DOCUMENTS

| | | | |
|---|---|---|---|
| 5,463,973 A * | 11/1995 | Tait | F16M 13/02 116/173 |
| 5,627,311 A * | 5/1997 | Nakaya et al. | 73/147 |
| 6,622,649 B1 | 9/2003 | Shaw et al. | |
| 2004/0229988 A1* | 11/2004 | Thai et al. | 524/425 |
| 2005/0069415 A1 | 3/2005 | Ferracani et al. | |
| 2009/0320733 A1 | 12/2009 | Stein et al. | |
| 2011/0133460 A1 | 6/2011 | Cucci et al. | |

FOREIGN PATENT DOCUMENTS

JP    2002278489 A  *  9/2002

OTHER PUBLICATIONS

BannerFlex Wind Tunnel Test, http://bannerflexeurope.com/tunnel.asp, 2007.*

* cited by examiner

*Primary Examiner* — Paul West
(74) *Attorney, Agent, or Firm* — Thorpe, North & Western L.L.P.

(57) ABSTRACT

The present disclosure is drawn to an air flow device and system for evaluating fabric integrity and cyclic stress of a media banner, and a method of simulating prolonged wind exposure on a media banner. The device can comprise a duct having an exit opening with an opening area of 100 to 250 in$^2$; a blower in fluid communication with the duct, the blower and the duct adapted to generate an ambient air speed at the exit opening of 35 mph or more, wherein the exit opening is positioned at least 2 feet from the blower; and a programming panel electrically coupled with the blower and adapted to program and cycle operation times and air speeds.

17 Claims, 3 Drawing Sheets

AIR FLOW DEVICE

BACKGROUND

The demand for digital media material with green or environmentally friendly construction is in shortage in the signage market today. For example, very strong banners can be constructed from vinyl material, which can negatively impact the environment. On the other hand, banners constructed from green materials can be environmentally friendly, but often are not as strong and wind resistant as traditional vinyl banners. With the use of many newer materials for the preparation of banners, these materials are not time tested in real world situations, e.g., outdoors for prolonged periods of time under windy conditions. Short of conducting long-term, outdoor testing with unpredictable weather conditions, or using expensive wind tunnel testing each time a new material is prepared, there is not a quick and reliable way of testing these materials with respect to long term exposure to the wind and other elements.

BRIEF DESCRIPTION OF THE DRAWINGS

Features and advantages will be apparent from the detailed description which follows, taken in conjunction with the accompanying drawings, which together illustrate, by way of example, features of the disclosure.

Figure 1:
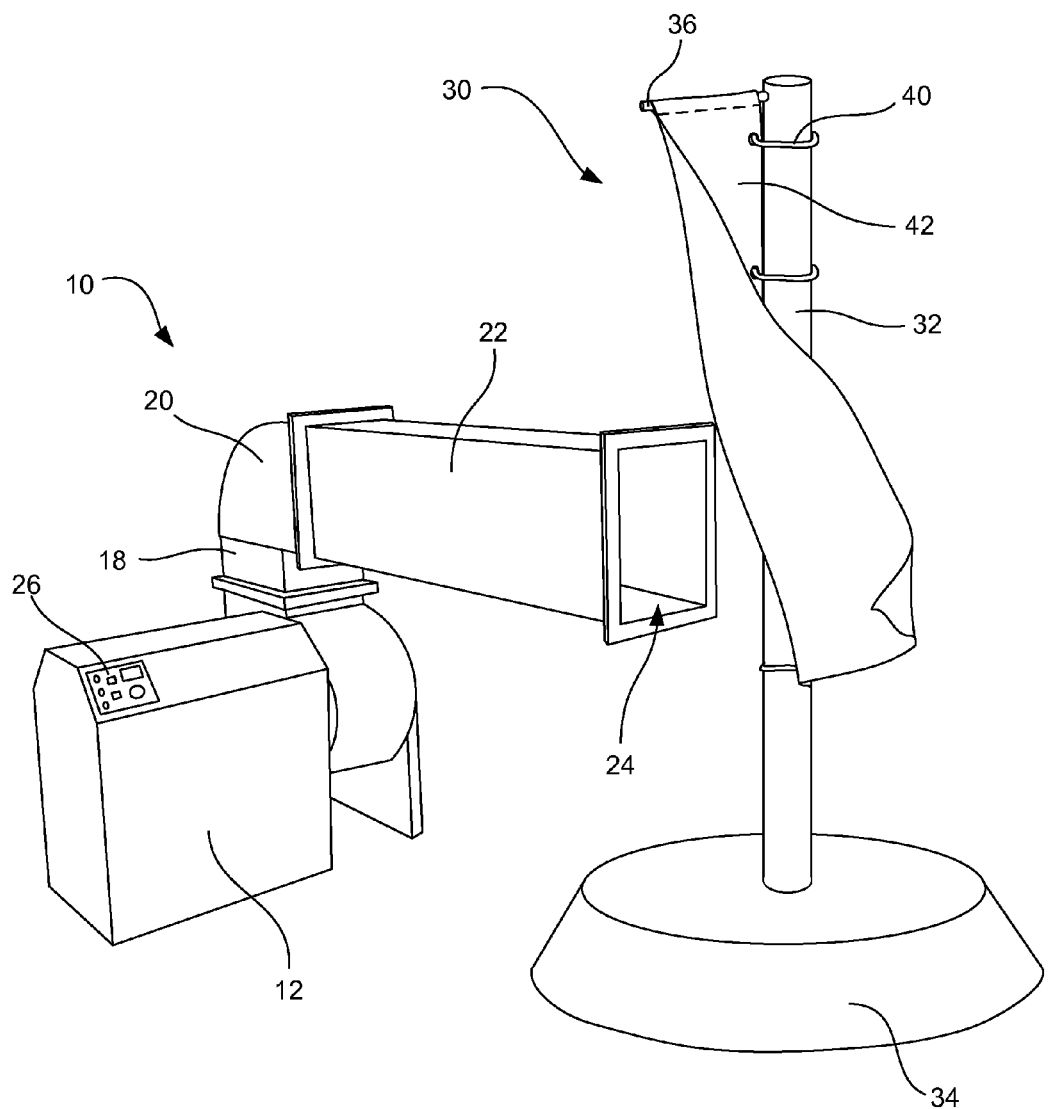
FIG. 1 is a perspective view of an air flow device for evaluating fabric integrity and cyclic stress of a media banner used in conjunction with a one pole banner stand in accordance with examples of the present disclosure.

Reference will now be made to the exemplary embodiments illustrated, and specific language will be used herein to describe the same. It will nevertheless be understood that no limitation of the scope of the disclosure is thereby intended.

DETAILED DESCRIPTION

In accordance with the FIGS. and other general description herein, air flow devices, systems, and methods are set forth for evaluating fabric integrity and cyclic stress of a media banner by simulating prolonged wind exposure to the banner in a quick an efficient manner. More specifically, an air flow device for evaluating fabric integrity and cyclic stress on a media banner can comprise a duct, a blower, and a programming panel. The duct can include an exit opening having an opening area of 100 to 250 in$^2$. The blower can be in fluid communication with the duct such that the blower and the duct are collectively adapted to generate an ambient air speed within 4 inches of the exit opening of 35 mph or more. Furthermore, to avoid contact between a banner being tested and a fan or other mechanical device that may be present on the blower, the exit opening can be positioned at least 2 feet from the blower. Furthermore, the programming panel can be electrically coupled with the blower and adapted to program and cycle operation times and air speeds 35 mph or more.

In another example, a system for evaluating fabric integrity and cyclic stress of a media banner can comprise an air flow device and a banner pole. The banner pole can be configured to support a top portion of the media banner, and can be coupled to a banner stand or other vertical pole used to support the media banner. The air flow device can include a duct having an exit opening with an opening area of 100 to 250 in$^2$, and a blower in fluid communication with the duct, the blower and the duct adapted to generate an ambient air speed within 4 inches of the exit opening of 35 mph or more. As mentioned, the banner pole can be part of a banner stand or other banner hanging system that hangs the media banner along multiple adjacent edges of the media banner, wherein one or more edge remains free and unsecured.

In another example, a method of simulating prolonged wind exposure on a media banner can comprise securing a media banner to a fixed structure along multiple adjacent edges of the media banner, wherein one or more edge remains free and unsecured. Another step can include applying forced ambient air to the media banner at an air speed ranging from 25 to 45 mph for a period of time that simulates one or more weeks of outdoor wind exposure having an average outdoor wind speed of 10 mph or more.

It is noted that when discussing the present devices, systems, and methods, each of these discussions can be considered applicable to each of these examples, whether or not they are explicitly discussed in the context of that example. Thus, for example, in discussing a duct with respect to the device, that discussion is also applicable to the systems and the methods, and vice versa.

Figure 2:
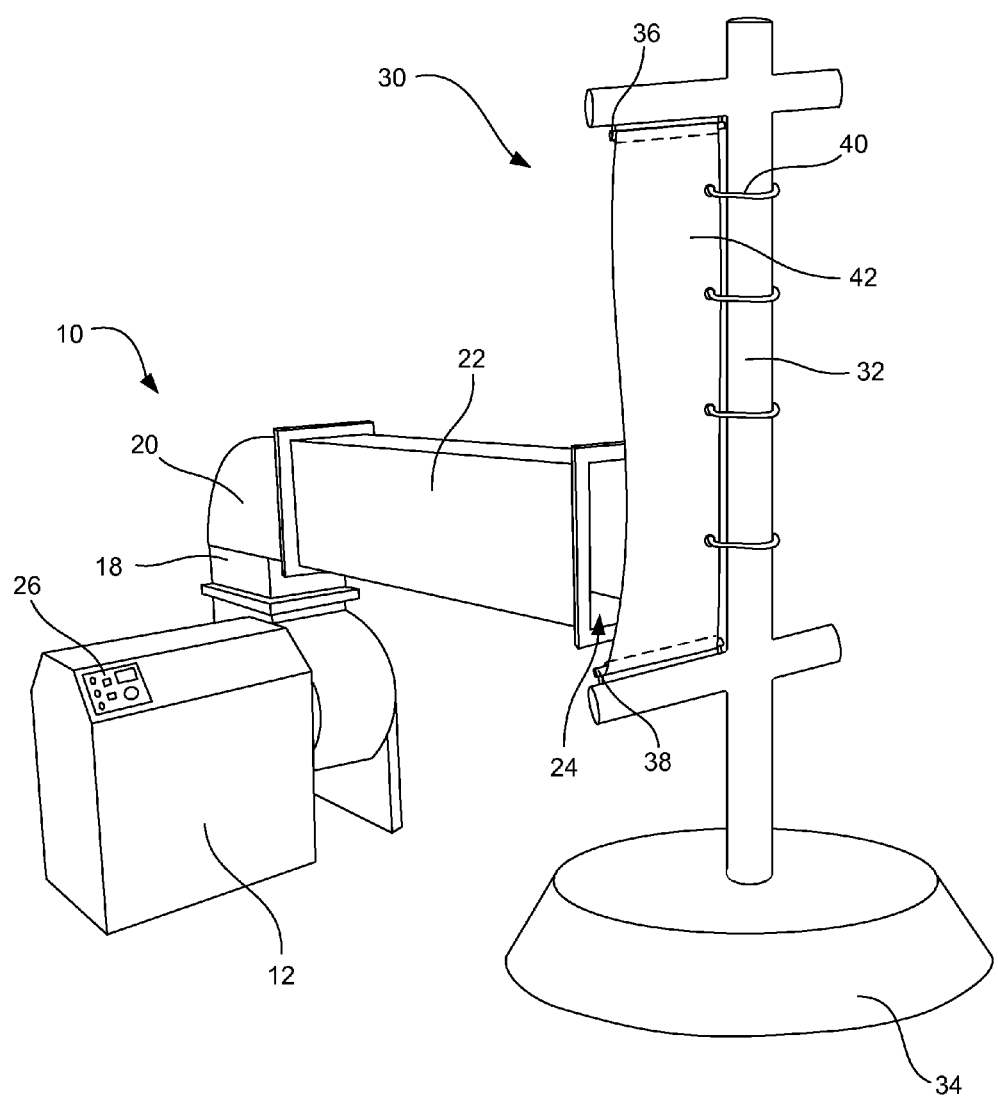
FIG. 2 is a perspective view of an air flow device for evaluating fabric integrity and cyclic stress of a media banner used in conjunction with a two pole banner stand in accordance with examples of the present disclosure.

Turning now to the FIGS., further detail is provided with respect to the air flow devices, systems, and methods described herein. Referring to FIGS. 1 and 2, for example, an air flow device 10 and system 10, 30 for evaluating fabric integrity and cyclic stress of a media banner is shown. Specifically, a blower 12 including a motor and a fan (not shown in FIGS. 1 and 2, but shown in FIG. 3) is configured to force ambient air at high velocity through a first duct 18 to a second duct 22 through an elbow duct 20. This configuration is merely exemplary, as there is no requirement that the air flow be sent through an elbow, nor is there a requirement that only a single bend in the duct system be present. Any arrangement of blower and ducting can be used provided the air flow parameters set forth herein can be met. In this example, the exit opening 24 is rectangular in shape, though any other shape can be used, including square, oval, round, etc.

The air flow device 10 also includes a programming panel 26 electrically coupled to the motor and/or the fan to control the timing of the air flow, the velocity of the air flow, or any other parameter desired for use in accordance with examples of the present disclosure. For example, the device can be adapted and programmed to cycle operation times and air speeds ranging from 5 mph to 45 mph, from 10 to 35 mph, or any other parameters desired by the operator within limits allowable by the device configuration. The air speed, for example, can be controlled by the use of a Variable Frequency Device (VFD) that can adjust the wind velocity. To illustrate, the device can be configured to apply forced ambient air to the media banner at an air speed ranging from 25 to 45 mph for a period of time that simulates one or more weeks of outdoor wind exposure having an average wind speed of 10 mph or more, 20 mph or more, etc. In one example, the air speeds can be programmed to maintain an air speed of 30 to 40 mph (e.g., about 35 mph) for a period of an hour or more, so as to simulate a least one week of ambient wind velocity.

In addition to the air flow device 10 described above, the system 10, 30 can further include a banner standard 30, which in this example is free standing. It is to be understood that the banner standard can be integrated into existing structures, such as buildings, light poles, or the like. This specific arrangement of a free-standing banner standard is merely exemplary. The banner standard can be configured as shown in FIG. 1 as a one (horizontal) pole stand, or as shown in FIG. 2 as a two (horizontal) pole stand. In both cases, by example, the banner standard includes a base 34 that supports a post or side structure 32. In the one pole arrangement, the side structure supports a top cross bar or banner pole 36, and in the two pole arrangement, the side structure supports both a top cross bar (banner pole) and a bottom cross bar (second banner pole) 38. Thus, the flag or banner 42 is either supported on the top (by the banner pole) and one side using a tie and eyelet system 40 as per the one pole arrangement (FIG. 1), or is supported on the top and bottom (by the banner pole and second banner pole) and the side using the tie and eyelet system as per the two pole arrangement (FIG. 2). It is noted that in FIG. 2, the side structure includes both a vertical portion and two horizontal portions, whereas in FIG. 1, only a vertical portion is present. Either arrangement is usable in accordance with examples of the present disclosure. In both arrangements, at least one side of the media banner is free to move or whip in response to the high velocity air flow provided by the air flow device.

Figure 3:
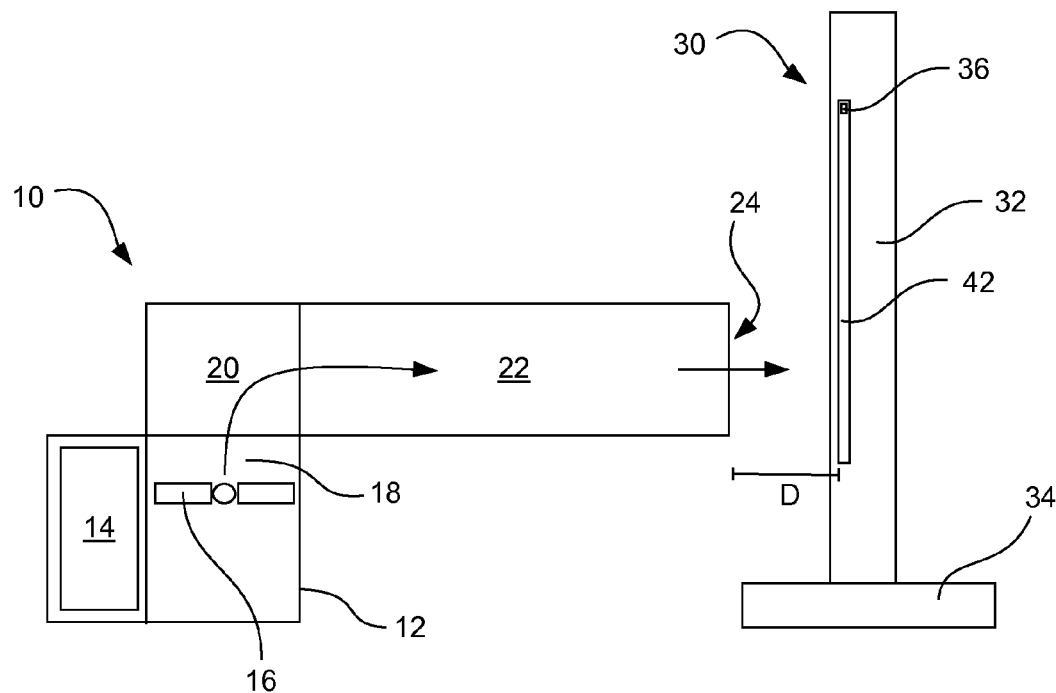
FIG. 3 is a schematic view of a air flow device for evaluating fabric integrity and cyclic stress of a media banner used in conjunction with a banner stand in accordance with examples of the present disclosure.

FIG. 3 provides a schematic representation of an example device described herein. As previously described, the air flow device 10 or system 10, 30 includes a blower 12 that supports the device as a whole, as well as a motor 14 and a fan 16. A first duct 18, an elbow duct 20, and a second duct 22 are also shown in this example, though this arrangement is merely exemplary. The exit opening 24 is shown where the air flow generated by the motor, fan, and ducting exits the air flow device at an area and velocity suitable for testing banners or flags in accordance with examples of the present disclosure. Regarding the system specifically, the banner standard 30 in this example includes a base 34, a post or side structure 32, and a banner pole or top crossbar 36 supporting a banner or flag 42, all as previously described with respect to FIGS. 1 and 2. In this example, however, the banner or flag is shown at a distance D from the exit opening of the duct. In accordance with examples of the present disclosure, this distance can be any distance that can cause stress to the fabric of the banner, but in one example, this distance D can be from 1 to 8 inches when the banner is at rest (prior to beginning air flow on the banner). In another example, this distance can be from 2 to 6 inches, and in still another example, the distance can be about 4 inches. It is noted that air flow from the air flow device is typically measured at 4 inches from the exit opening, and it turns out that about 4 inches is a good distance to achieve maximum banner whipping in response to the high air flow described herein.

Controlling the size relationship between the media banner 42 and the exit opening 24 of the air flow device 10 can also be used to maximize or speed up simulation times. For example, the media banner can have a banner area, and the banner area to exit opening area can be at an area size ratio from 2:1 to 10:1, or from 3:1 to 8:1 in another example. Exemplary opening areas that can be used range from 100 to 250 in$^2$, though this will depend on the size of the media banner. For example, a rectangular exit opening area of 10 inches by 14 inches (140 in$^2$) may be a suitable size for a banner that is 47 inches tall by 27 inches wide (1269 in$^2$), which provides a media banner to exit opening area ratio of about 9:1. Alternatively, if the media banner is 28 inches tall by 18 inches wide (504 in$^2$), then the ratio is greater than 3:1. By controlling the ratio size in this manner, a greater degree of media banner whipping can be achieved than with size ratios outside of these parameters. That being stated, size ratios outside of this range are also within the scope of the present disclosure. Furthermore, by securing the media banner to at least two adjacent sides of the banner standard, the media banner does not spend too much time flipping away from the air flow at the exit opening, thus also increasing the whipping cycles of the media banner per time interval.

Figure 4:
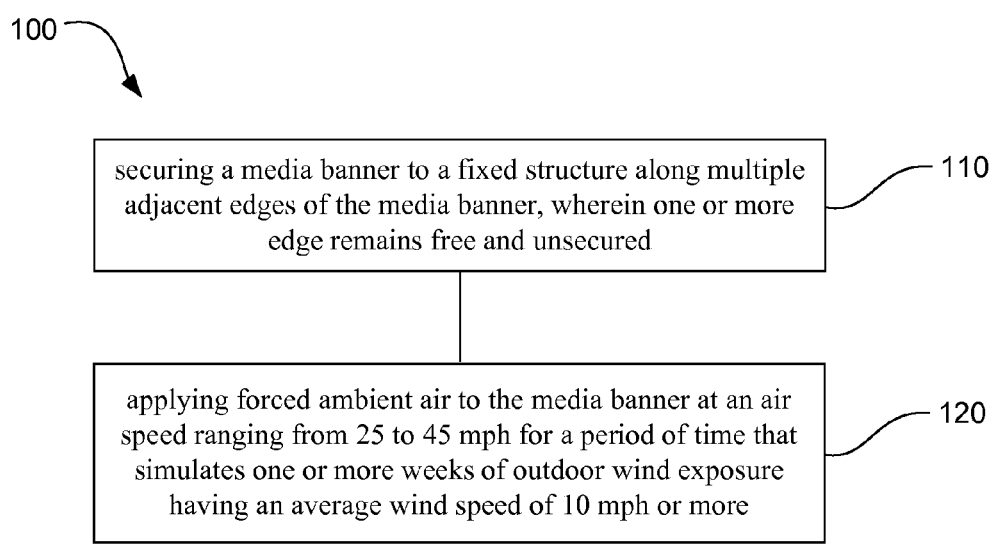
FIG. 4 is a flow diagram illustrating a method in accordance with examples of the present disclosure.

Turning now to FIG. 4, a method 100 of simulating prolonged wind exposure on a media banner can comprise securing 110 a media banner to a fixed structure along multiple adjacent edges of the media banner, wherein one or more edge remains free and unsecured. Another step can include applying 120 forced ambient air to the media banner at an air speed ranging from 25 to 45 mph for a period of time that simulates one or more weeks of outdoor wind exposure having an average wind speed of 10 mph or more. In one specific example, the air speed can range from 30 to 40 mph.

In this method, the media banner can be constructed of any of a number materials, such as High Density Polyethylene (HDPE), woven products of polyethylenes or polyesters, ethylene vinyl alcohols, ethylene vinyl acetate (EtVA), polypropylene, polyolefins, or the like. For example, the banner might be constructed of a woven HDPE with an EtVA coating applied to one or both sides thereof. Furthermore, the media banner can be configured to have a banner area that corresponds to the exit opening where the forced air is ejected at a banner area to exit opening area at a size ratio from 2:1 to 10:1, or from 4:1 to 8:1, as previously discussed. Furthermore, the exit opening can be positioned at from 1 to 8 inches from the media banner, or from 2 to 6 inches from the media banner, or at about 4 inches from the media banner to generate a maximum amount of media flag whipping.

In accordance with these and other examples, the test device, system and method described herein can be designed uniquely based on several factors to perform a severe wind test on a media to predict the actual performance and durability of the media in a real time outdoor environment. In other words, this equipment can be used to perform testing to predict the type of media that may be effective for used as a draped banner or flag, particularly outdoors. To achieve this, the user can test the time and air velocity that an object can tolerate before it degrades.

There are several advantages to using the devices, systems, and methods of the present disclosure. In some examples, the size of the air flow device or the system described herein can be a manageable size that the can be operated and moved by a single person, and thus, unlike a large wind tunnel room, can be used and moved conveniently in a factory or lab. Furthermore, the air flow device described herein can be used effectively to test and correlate failure data to real time outdoor performance, providing correlated values that can be used to predict the performance of the flag or banner in real time. For example, with respect to the use of a certain flag or banner made from a specific formulation of woven High Density Polyethylene (HDPE), a system as described herein (e.g., 27×47 inch banner, one pole arrangement, 10×14 inch exit opening, 35 mph air flow, 4 inch distance between exit opening an banner, and 1 hour of time) may generate a 1 hour failure of the banner that would normally have taken 1 week (at an average of 20 mph wind) of outdoor observation to achieve. Thus, for this specific HDPE material under these testing conditions, a 1 hour to 1 week correlation to failure can be used as a baseline for testing similar materials. These types of correlations can be used to predict how long a media banner will last in a windy outdoor environment, or alternatively, can be used merely to confirm that at least a specified period of outdoor time can be guaranteed, e.g., the banner will last at least a year outdoors, etc.

It is noted that, as used in this specification and the appended claims, the singular forms "a," "an," and "the" include plural referents unless the context clearly dictates otherwise.

The term "banner" or "flag" are used interchangeably herein.

The term "banner stand" or "banner standard" includes both a side a side support structure (which can be an existing structure or a freestanding pole, for example) used in combination with a banner pole or top crossbar as shown in FIG. 1. Typically, the banner pole is secured to the side support structure so that adjacent edges of the media banner can be secured, while another edge or multiple edges remain free to flow or whip in the wind. The banner standard can optionally include a second banner pole or bottom crossbar, as shown in FIG. 2.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 wt % to about 5 wt %" should be interpreted to include not only the explicitly recited values of about 1 wt % to about 5 wt %, but also include individual values and sub-ranges within the indicated range. Thus, included in this numerical range are individual values such as 2, 3.5, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

EXAMPLES

The following examples illustrate embodiments of the disclosure that are presently known. Thus, these examples should not be considered as limitations of the disclosure.

Example 1

Air Flow Device

An air flow device was built similar to that shown in FIGS. 1-3 having a blower including a motor and a fan, as well as ducting suitable for blowing air therefrom at a wind velocity of up to about 40-45 mph (as measured four inches outside of the exit opening using a velometer). The exit opening on this particular air flow device was about 10 inches by 14 inches in size. The air flow device included a Variable Frequency Device (VFD) to adjust the wind velocity. Specifically, certain selected frequencies shown in Table 1 were used to achieve the following air flow velocities as measured by the velometer:

TABLE 1

| Frequency (Hz) | Air Velocity (MPH) |
|---|---|
| 60 | 38 |
| 50 | 34 |
| 40 | 25 |
| 30 | 19 |
| 25 | 17 |
| 20 | 13 |
| 15 | 10 |

Example 2

One Pole Media Banner Construction

Media banners were prepared using a high density polyethylene (HDPE) woven scrim (74 gsm) coated on a first side with a 38 gsm tie layer and a 25 gsm ethyl vinyl alcohol layer (which would act as the inkjet ink receiving layer). The opposite side of the woven scrim was also coated with the same coatings as the first side, making the media printable on both sides. A first media banners size was prepared by cutting the coated woven scrim down to a size of 27 inches (wide) by 47 inches (tall), thus leaving an unfinished edge. A second media banner size was prepared that was 36 inches (wide) by 120 inches (tall), also leaving an unfinished edge. In each case, a 2.5 inch wide sleeve was formed along top edge so that a banner pole or rod could be inserted into a top sleeve, thus, allowing the media banner to be hung vertically from top to bottom. Additionally, the media was tied to a side structure (which in this case was a side pole) along one of the elongated sides using grommets and zip ties. This configuration is shown generally in FIG. 1.

Example 3

Simulated Air Flow Evaluation for One Pole Media Banner

The first media banner (smaller size) prepared in accordance with Example 2 was placed four inches directly in front of the air flow device of Example 1, and the air flow device was configured to blow ambient air at 35 mph for a total of 1 hour. At end of the one hour test, the unsecured banner corner was shredded and all the woven tapes became loose. Also, the surface of the media banner showed lines of cracks and scratches due to a wipping flip-flap effect of the strong air flow.

Example 4

Outdoors Ambient Air Flow Evaluation for One Pole Media Banner

The second media banner (larger size) prepared in accordance with Example 2 was evaluated in a real time test environment by hanging the media banner outside where the average wind speed during a week was about 20 mph. This particular banner was printed on both sides with inkjet images, and was hung from a parking lot light pole as the side structure. A banner pole was affixed to the parking lot light pole to give the banner a top cross support as well, similar to that shown in FIG. 1. The banner was monitored twice a week by observing the integrity of the banner and by measuring the natural wind speed. This banner failed with a similar failure profile as that described in Example 3 in about one week of real time. Thus, a rough correlation of 1 week in a real world example to 1 hour using a simulated air flow device was ascertained to be reasonable for this material under these conditions.

Example 5

Two Pole Media Banner Construction

The same two media banners described in Example 2 were prepared, however, in this Example, two 2.5 inch wide sleeve were formed along the top and the bottom so that a banner pole (top crossbar) could be inserted into a top sleeve and a second banner pole (bottom crossbar) could be inserted into a bottom sleeve, thus, securing the media banner on three sides. Specifically, the media banner was secured along a top and bottom edge using the two banner poles, and along the one of the longer sides using grommets and zip ties. This configuration is shown generally in FIG. 2.

Example 6

Simulated Air Flow Evaluation for Two Pole Media Banner

The first media banner (smaller size) prepared in accordance with Example 5 was placed four inches directly in front of the air flow device of Example 1, and the air flow device was configured to blow ambient air at 35 mph for a total of 15 hours. At end of the 15 hour test, the free edge (long side not secured to the vertical pole) remained in good condition. Longer times of testing, e.g., 50 hours, may lead to damage to the unsecured free edge of the flag when configured using two horizontal poles and a single vertical pole, such as shown in FIG. 2.

Example 7

Outdoors Ambient Air Flow Evaluation for Two Pole Media Banner

The second media banner (larger size) prepared in accordance with Example 5 was evaluated in a real time test environment by hanging the media banner outside where the average wind speed during a 6 month period was about 20 mph. Two banner poles (upper and lower) were affixed to a parking lot light pole to give the banner a top support as well as a side support as described in Example 2. The banner was monitored twice a week by observing the integrity of the banner and by measuring the natural wind speed. The banner in this large dimension likewise remained in good condition.

Example 8

Results

With respect to the one pole configurations as shown in FIG. 1 and described in Examples 3 and 4, a ratio of about 1 hour simulated conditions to 1 week real conditions (e.g., very windy outdoor environment) appears reasonable. Thus, failure of a given media banner can be predicted for an outdoor windy environment in a matter of hours using the devices, systems, and methods described herein. With respect to the two pole configurations, longer outdoor environment times can be confirmed provided the user hangs the media banner outdoors in the two pole (i.e. two crossbar) configuration as shown in FIG. 2. This is verifiable as a real time test 6 months and correlates to at least 15 hours of simulated wind using the devices, systems, and methods described herein.

Example 9

Alternative Media Banner Evaluation

The same tests were repeated as described in Examples 2-4 above using different materials of woven polyester fabric with a tighter weave count per inch. More specifically, the textile material made of polyester fabric weaves constructed in three layers of fabric, and stitched on the edge perimeters with a sewing machine to form a three layered banner with thread-secured edges. The flag sizes used for the simulated air flow test and the outside real time test were the same. This banner was subjected to 35 mph air flow using one pole assembly for 50 hours. The banner survived the 50 hour winds test due in part to the thread-secured edges. Thus, based on the rough correlations described in Example 8 above, this banner can likely be guaranteed to last outdoor for more than one year. To support this assertion, larger banner that was being tested outdoors in a real world environment has been hanging outdoors in a parking lot for more than 6 months with no signs of wind damage.

While the invention has been described with reference to certain examples, those skilled in the art will appreciate that various modifications, changes, omissions, and substitutions can be made without departing from the spirit of the disclosure. It is intended, therefore, that the disclosure be limited only by the scope of the following claims.

What is claimed is:

1. An air flow device for evaluating fabric integrity and cyclic stress of a media banner, comprising:
   a duct having an exit opening with an opening area of 100 to 250 in$^2$;
   a blower in fluid communication with the duct, the blower and the duct adapted to generate an ambient air speed within 4 inches of the exit opening of 35 mph or more, wherein the exit opening is positioned at least 2 feet from the blower, wherein the duct has a uniform cross-sectional area from the blower to the exit opening, and wherein air flow generated by the blower exits the air flow device at the exit opening; and
   a programming panel electrically coupled with the blower and adapted to program and cycle variable operation times and variable air speeds including the air speed of 35 mph or more.

2. The air flow device of claim 1, wherein the programming panel is further adapted to program and cycle operation times and air speeds ranging from 5 mph to 45 mph.

3. A system for evaluating fabric integrity and cyclic stress of a media banner, comprising:
   an air flow device, including:
      a duct having an exit opening with an opening area of 100 to 250 in$^2$, and a blower in fluid communication with the duct, the blower and the duct adapted to generate an ambient air speed at the exit opening of 35 mph or more; and a banner pole adapted to secure to a side structure, wherein the banner pole supports a top portion of a media banner and the side structure supports a side portion of the media banner, wherein the top portion and the side portion comprise multiple adjacent edges of the media banner so that the media banner is secured to a fixed structure along the multiple adjacent edges of the media banner, and wherein the wherein one or more edge of the media banner remains free and unsecured.

4. The system of claim 3, wherein the banner pole is adapted to hang the media banner at from 1 to 8 inches from the exit opening.

5. The system of claim 3, wherein the air flow device further comprises a programming panel electrically coupled with the blower and adapted to program and cycle operation times and air speeds ranging from 5 mph to 45 mph.

6. The system of claim 3, wherein the air flow device is adapted to apply forced ambient air to the media banner at an air speed ranging from 25 to 45 mph for a period of time that simulates one or more weeks of outdoor wind exposure having an average wind speed of 10 mph or more.

7. The system of claim 3, further comprising a second banner pole adapted to secure to the side structure, wherein the second banner pole supports a bottom portion of the media banner.

8. The system of claim 3, wherein the banner pole and the side structure is adapted to hang a media banner having a banner area with a banner area to opening area of the duct ratio from 2:1 to 10:1.

9. The system of claim 3, wherein the duct has a uniform cross-sectional area from the blower to the exit opening, and wherein air flow generated by the blower exits the air flow device at the exit opening.

10. The system of claim 3, wherein the exit opening is positioned at least 2 feet from the blower.

11. A method of simulating prolonged wind exposure on a media banner, comprising:

securing a media banner to a fixed structure along multiple adjacent edges of the media banner, wherein one or more edge remains free and unsecured; and applying forced ambient air to the media banner at an air speed ranging from 25 to 45 mph for a period of time that simulates one or more weeks of outdoor wind exposure having an average wind speed of 10 mph or more, wherein the media banner has a banner area and the forced ambient air is ejected from a duct having an exit opening with an opening area of 100 to 250 $in^2$, and wherein the banner area to opening area has an area size ratio from 2:1 to 10:1.

12. The method of claim 11, wherein the media banner is a woven media banner comprising high density polyethylene, low density polyethylene, polypropylene, polyolefin, or mixture thereof.

13. The method of claim 11, wherein the air speed is from 30 to 40 mph.

14. The method of claim 11, wherein the media banner is secured to the fixed structure along two adjacent edges in a one pole arrangement.

15. The method of claim 11, wherein the media banner is secured to the fixed structure along three adjacent edges in a two pole arrangement.

16. The method of claim 11, wherein the area size ratio is from 4:1 to 8:1.

17. The method of claim 11, wherein the exit opening is positioned at from 1 to 8 inches from the media banner.

* * * * *